United States Patent [19]

Ward et al.

[11] Patent Number: 4,621,089

[45] Date of Patent: Nov. 4, 1986

[54] PYRAZOLOPYRIDINE DERIVATIVES AND THEIR USE IN TREATING INFLAMMATION AND ALLERGIC CONDITIONS

[75] Inventors: Robert W. Ward, Old Harlow; Ian Hughes, Sawbridgeworth, both of England

[73] Assignee: Beecham Group p.l.c., Brentford, England

[21] Appl. No.: 704,621

[22] Filed: Feb. 22, 1985

[30] Foreign Application Priority Data

Feb. 22, 1984 [GB] United Kingdom ................ 8404586

[51] Int. Cl.$^4$ .................... A61K 31/44; C07D 471/04
[52] U.S. Cl. .................................. 514/303; 546/119; 546/120
[58] Field of Search ................ 546/119, 120; 514/303

[56] References Cited

PUBLICATIONS

E. Ajello, "New Syntheses of Condensed Heterocycles from Isoxazole Derivatives. II. Pyrazolo [4,3-b] Pyridine," *J. Heterocycl. Chem.*, 1971, 8 (6), 1035–37.
F. M. Dietrich and R. Hess, "Hypersensitivity in Mice," *Int. Arch. Allergy*, 38: 246–259 (1970).
H. E. Foster and J. Hurst, "Pyrazolopyridines. Part IV. Preparation and Tantomerism of 6-Cyano- and 6-Ethoxycarbonyl-1,4-dihydropyrazolo[4,3-b]pyridin-7-ones", *J. Chem. Soc.—Perkin Translation I,* 1976 (5), 507.
B. A. Jakschik et al., "Calcium Stimulation of a Novel Lipoxygenase," *Biochemical and Biophysical Research Communickations,* 95: 103–110 (1980).
R. W. Middleton et al., "N-Methylation of Heterocycles with Dimethylformamide Dimethyl Acetal," *Synthesis* (1984) 740.
K. F. Swingle et al., "Comparison of Croton Oil and Cantharidin Induced Inflammations of the Mouse Ear and Their Modification by Topically Applied Drugs," *Arch. Int. Pharmacodyn.* (1981) 254: 168–176.
Chemical Abstracts, 87:168030e, Nov. 21, 1977.

*Primary Examiner*—Henry R. Jiles
*Assistant Examiner*—Bernard I. Dentz
*Attorney, Agent, or Firm*—James F. Haley, Jr.; Paul H. Ginsburg; David K. Barr

[57] ABSTRACT

Compounds of formula (I) and pharmaceutically acceptable salts thereof:

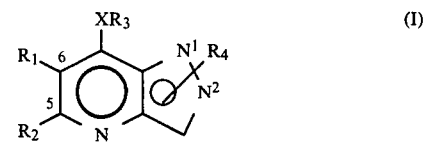

wherein:

X is NR wherein R is hydrogen or $C_{1-6}$ alkyl, oxygen, sulphur, SO or $SO_2$;

$R_1$ is $COR_5$ wherein $R_5$ is hydroxy, or $COR_5$ is a pharmaceutically acceptable ester or amide group; or $CF_3$; and $R_2$ is hydrogen, $C_{1-6}$ alkyl or phenyl optionally substituted by halogen, $CF_3$, $C_{1-4}$ alkoxy or $C_{1-4}$ alkyl; or $R_2$ is $COR_5$ as defined or $CF_3$ and $R_1$ is hydrogen;

$R_3$ is $C_{1-10}$ alkyl, optionally substituted by hydroxy, $C_{1-4}$ alkoxy, thiol, $C_{1-4}$ alkylthio or $NR_6R_7$ wherein $R_6$ and $R_7$ are independently hydrogen or $C_{1-6}$ alkyl or together are $C_{3-6}$ polymethylene; $C_{2-10}$ alkenyl or phenyl optionally substituted by one or two of halogen, $CF_3$, $C_{1-4}$ alkoxy, $C_{1-4}$ alkyl, hydroxy, nitro, cyano, $C_{2-10}$ acyloxy, $NR_8R_9$ wherein $R_8$ and $R_9$ are independently selected from hydrogen, $C_{1-6}$ alkyl, $C_{2-7}$ alkanoyl or $C_{1-6}$ alkylsulphonyl or $COR_{10}$ wherein $R_{10}$ is hydroxy, $C_{1-6}$ alkoxy or $NR_{11}R_{12}$ wherein $R_{11}$ and $R_{12}$ are independently selected from hydrogen or $C_{1-6}$ alkyl; and $R_4$ is hydrogen; or $C_{1-4}$ alkyl or benzyl attached at nitrogen atom 1 or 2 having anti-inflammatory and/or anti-allergy activity, a process for their preparation and their use as pharmaceuticals.

9 Claims, No Drawings

PYRAZOLOPYRIDINE DERIVATIVES AND THEIR USE IN TREATING INFLAMMATION AND ALLERGIC CONDITIONS

The present invention relates to pyrazolopyridines having useful pharmacological activity, to a process for their preparation and to their use as anti-inflammatories.

J. Heterocycl. Chem. 1971, 8(6), 1035–7 discloses compounds of the formula (A):

wherein R is $NH_2$, OH, $NAc_2$ or Cl. The compound wherein R is $NAc_2$ is described as having CNS antidepressant activity in mice.

A structurally distinct group of pyrazolopyridine derivatives have now been discovered which compounds have anti-inflammatory (including anti-rheumatic) and/or anti-allergy activity.

Accordingly, the present invention provides a compound of the formula (I) and pharmaceutically acceptable salts thereof:

wherein:

X is NR wherein R is hydrogen or $C_{1-6}$ alkyl, oxygen, sulphur, SO or $SO_2$;

$R_1$ is $COR_5$ wherein $R_5$ is hydroxy, or $COR_5$ is a pharmaceutically acceptable ester or amide group; or $CF_3$; and $R_2$ is hydrogen, $C_{1-6}$ alkyl or phenyl optionally substituted by halogen, $CF_3$, $C_{1-6}$ alkoxy or $C_{1-4}$ alkyl; or $R_2$ is $COR_5$ as defined or $CF_3$ and $R_1$ is hydrogen;

$R_3$ is $C_{1-10}$ alkyl, optionally substituted by hydroxy, $C_{1-4}$ alkoxy, thiol, $C_{1-4}$ alkylthio or $NR_6R_7$ wherein $R_6$ and $R_7$ are independently hydrogen or $C_{1-6}$ alkyl or together are $C_{3-6}$ polymethylene $C_{2-10}$ alkenyl or phenyl optionally substituted by one or two of halogen, $CF_3$, $C_{1-4}$ alkoxy, $C_{1-4}$ alkyl, hydroxy, nitro, cyano, $C_{2-10}$ acyloxy, $NR_8R_9$ wherein $R_8$ and $R_9$ are independently selected from hydrogen, $C_{1-6}$ alkyl, $C_{2-7}$ alkanoyl or $C_{1-6}$ alkylsulphonyl or $COR_{10}$ wherein $R_{10}$ is hydroxy, $C_{1-6}$ alkoxy or $NR_{11}R_{12}$ wherein $R_{11}$ and $R_{12}$ are independently selected from hydrogen or $C_{1-6}$ alkyl; and $R_4$ is hydrogen; or $C_{1-4}$ alkyl or benzyl attached at nitrogen atom 1 or 2.

Suitable values for X include those wherein R in NR is hydrogen, methyl, ethyl, n- and iso-propyl, preferably hydrogen; and oxygen or sulphur. Favourably X is NH.

Suitable values for $R_1/R_2$ when $COR_5$ include $COR_5^1$ wherein $R_5^1$ is hydroxy, $C_{1-6}$ alkoxy, $C_{2-6}$ alkenyloxy, phenoxy or benzyloxy wherein the phenyl/benzyl moiety is optionally substituted by one or two of halogen, $CF_3$, $C_{1-4}$ alkoxy and $C_{1-4}$ alkyl; or $R_5^1$ is $NR_{13}R_{14}$ wherein $R_{13}$ and $R_{14}$ are independently hydrogen, $C_{2-6}$ alkyl, $C_{2-6}$ alkenyl, benzyl or phenyl optionally substituted as described above.

Examples of $R_5^1$ include hydroxy, methoxy, ethoxy, n- or iso-propoxy, amino, methylamino, dimethylamino, anilino and allylamino.

Suitable values for $R_2$ when other than $COR_5$ include hydrogen, methyl, ethyl, n- and iso-propyl and phenyl. Preferably $R_2$ is then hydrogen or methyl, usually hydrogen.

Preferably $R_1$ is $COR_5$.

Suitable values for $R_3$ include methyl, ethyl, n- and iso-propyl, n-, iso- sec- and tert-butyl, n-pentyl or $(CH_2)_nCH_3$ wherein n is 4 to 7, optionally substituted by methyl, ethyl and/or hydroxy, methoxy, n- or iso-propoxy, thiol, methylthio or amino optionally substituted by one or two methyl groups or by $C_4$ or $C_5$ polymethylene, vinyl, prop-1-enyl, prop-2-enyl, 1-methylvinyl, but-1-enyl, but-2-enyl, but-3-enyl, 1-methylenepropyl, 1-methylprop-1-enyl and 1-methylprop-2-enyl in their E and Z forms where stereoisomerism exists; or phenyl optionally substituted by one or two chloro, bromo, methoxy, ethoxy, n- and iso-propoxy, methyl, ethyl, n- and iso-propyl, n-, iso- sec- and tert-butyl, hydroxy, nitro, cyano, acetoxy, propionyloxy, benzyloxy, $NR_8^1R_9^1$ wherein $R_8^1$ and $R_9^1$ are independently selected from hydrogen, methyl, ethyl, n- and iso-propyl, acetyl, propionyl, methylsulphonyl and ethylsulphonyl; $COR_{10}^1$ wherein $R_{10}^1$ is hydroxy, methoxy, ethoxy, or $NR_{11}^1R_{12}^1$ wherein $R_{11}^1$ and $R_{12}^1$ are independently selected from hydrogen, methyl, n- and iso-propyl. Favourable values for $R_3$ include n-butyl, n pentyl, allyl, 2-methylallyl, 2-hydroxyethyl, 3-hydroxypropyl, 2-dimethylamino ethyl, 3-dimethylaminopropyl, phenyl and phenyl substituted by one of hydroxy, nitro, cyano, carboxy, t-butyl and ethoxycarbonyl in the 3- or 4-position.

Suitable values for $R_4$ include hydrogen, methyl, ethyl, n- and iso-propyl and benzyl. More suitably $R_4$ is hydrogen or 2-methyl. Favourably $R_4$ is hydrogen.

It will be appreciated that when $R_4$ is hydrogen the compounds of formula (I) exist as tautomers, i.e. the $R_4$ hydrogen atom is labile. The compounds wherein $R_4$ is hydrogen are therefore of formulae (IIa) and (IIb).

The compounds of the formula (I) can form acid addition salts with acids, such as the conventional pharmaceutically acceptable acids, for example hydrochloric, hydrobromic, phosphoric, acetic, fumaric salicylic, citric, lactic, mandelic, tartaric and methanesulphonic.

There is a group of compounds within formula (I) wherein either $R_1$ is hydrogen and $R_2$ is $COR_5'$ wherein $R_5'$ is hydroxy, $C_{1-6}$ alkoxy or $NR_{13}'R_{14}'$ wherein $R_{13}'$ and $R_{14}'$ are independently $C_{1-6}$ alkyl; or $CF_3$ or $R_1$ is $COR_5'$ or $CF_3$ and $R_2$ is hydrogen, $R_3$ is $C_{1-10}$ alkyl, $C_{2-10}$ alkenyl or phenyl optionally substituted as defined in formula (I), $R_4$ when other than hydrogen is attached at nitrogen atom 2 and the remaining variables are as defined in formula (I).

There is a favourable group of compounds within formula (I) of formula (III):

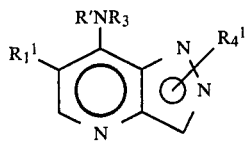

wherein $R_1{}^1$ is $COR_5{}^1$ as defined or $CF_3$, R40 is hydrogen or methyl, $R_4{}^1$ is hydrogen or 2-methyl, and $R_3$ is as defined in formula (I).

Suitable and preferred values for $R_1{}^1$, R', $R_4{}^1$ and $R_3$ are as described for the relevant variables under formula (I).

A favourable sub-group of compounds within formula (III) is of formula (IV):

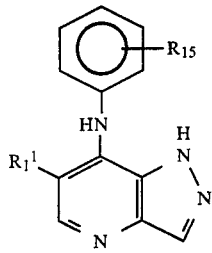

wherein $R_{15}$ is hydrogen, chloro, bromo, methoxy, ethoxy, hydroxy, cyano, carboxyl, ethoxycarbonyl, nitro or t-butyl.

Preferably $R_{15}$ when other than hydrogen is attached at the the 3- or 4-position, most preferably the 4-position.

A preferred sub-group of compounds within formula (III) is of formula (V):

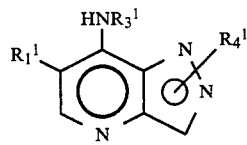

wherein $R_3{}^1$ is n-butyl, n-pentyl, allyl, 2-methylallyl, 2-hydroxyethyl, 3-hydroxypropyl, 2-thiolethyl, 2-methoxyethyl, 2-dimethylaminoethyl, 3-dimethylaminopropyl, 2-pyrrolidinoethyl or 3-pyrrolidinopropyl and $R_1{}^1$ and $R_4{}^1$ are as defined in formula (III).

Suitable and preferred values for the variables are as described for the relevant variables under formula (I).

A further group of compounds within formula (I) is of formula (VI):

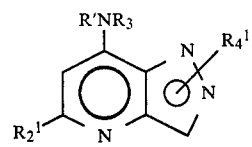

wherein $R_2{}^1$ is $COR_5{}^1$ as defined and the remaining variables are as defined in formula (III).

Suitable and preferred values for $R_2{}^1$, R', $R_3$ and $R_4{}^1$ are as described for the relevant variables under formula (I).

A preferred sub-group of compounds within formula (VI) is of formula (VII):

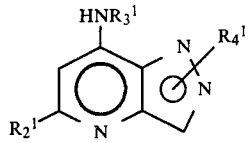

wherein $R_3{}^1$ and $R_4{}^1$ are as defined in formula (V) and $R_2{}^1$ is as defined in formula (VI).

Suitable and preferred values for the variables are as described for the relevant variables under formula (I).

Another sub-group of compounds within formula (I) is of formula (VIII):

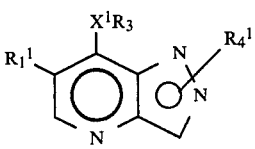

wherein $X^1$ is oxygen or sulphur, and $R_1{}^1$, $R_3$ and $R_4{}^1$ are as defined in formula (III).

Suitable and preferred values for $X^1$, $R_1{}^1$, $R_3$ and $R_4{}^1$ are as described for the relevant variables under formula (I).

The present invention also provides a process for the preparation of a compound of formula (I) or a pharmaceutically acceptable salt thereof, which process comprises the reaction of a compound of formula (IX):

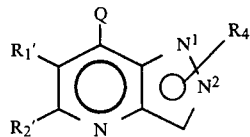

wherein Q is a leaving group, $R_1'$ and $R_2'$ are $R_1$ and $R_2$ or groups convertible thereto and $R_4$ is as defined in formula (I), with a compound of formula (X):

$$HX^2R_3' \qquad (X)$$

wherein $X^2$ is NR (as defined in formula (I)), oxygen or sulphur and $R_3'$ is $R_3$ or a group or atom convertible thereto; and thereafter optionally converting $X^2$ to X, $R_1'$ to $R_1$, $R_2'$ to $R_2$, $R_3'$ to $R_3$ and/or an $R_4$ hydrogen to an $R_4$ $C_{1-6}$ alkyl group and/or forming a pharmaceutically acceptable salt thereof.

Suitable leaving groups Q include halogens such as chloro and bromo, preferably chloro.

The reaction may be carried out under conventional conditions for nucleophilic aromatic displacements, at elevated temperatures using excess of reagent as solvent (eg aniline when X is NR) or in an inert solvent such as toluene, ethanol, dimethylformamide, dimethylsulphoxide, dioxan or water. The reaction preferably takes place in a sealed tube if $HX_2R_3'$ is of low boiling point.

Alternatively, when $X^2$ is oxygen or sulphur, the reaction may take place in the presence of a base, such as sodium hydride, potassium t-butoxide or sodium t-butoxide.

Compounds of formula (I) wherein X is SO or $SO_2$ may be prepared from the corresponding compounds wherein X is S by conventional oxidation methods, such as using sodium periodate or with one equivalent of m-chloroperbenzoic acid (to form the compound of formula (I) wherein X is SO) or two equivalents of m-chloroperbenzoic acid (to form the compound of formula (I) wherein X is $SO_2$).

Conversion of an R hydrogen in X to an R $C_{1-6}$ alkyl group may be carried out by conventional amine alkylation or acylation (e.g. formylation) followed by reduction.

An $R_5$ hydroxy group in $R_1$ or $R_2$ may be converted to an $R_5$ alkoxy group by conventional esterification procedures and an $R_5$ hydroxy group may be converted to an $NR_6R_7$ group by condensation and in the presence of a dehydrating agent, such as dicyclohexylcarbodiimide.

An $COR_5$ group when amide can be converted to a $COR_5$ ester group by conventional hydrolysis/esterification in ethanolic HCl. One $COR_5$ ester group may be converted to another $COR_5$ ester by conventional transesterification procedures. It will be appreciated that when $R_2$ is an ester group, reaction of the compound of formula (X) with the compound of formula (IX) may also substitute $R_5$, in which case subsequent conversion of $R_5$ is necessary as described above.

$R_1'$ or $R_2'$ may be methyl, in which case it may be converted to a $CO_2H$ group by conventional oxidation with an oxidising agent such as potassium permanganate. This conversion is preferably, however, carried out on the intermediate of formula (V) or at an earlier stage.

Conversions of $R_3$ phenyl substituents are generally known in the art of aromatic chemistry. Examples of such conversions are as follows:

(a) an hydroxy group may be converted to acyloxy by conventional acylation procedures, preferably using the acid anhydride in trifluoroacetic acid at elevated temperature;
(b) a cyano group may be converted to carboxy by base catalysed hydrolysis; preferably using sodium hydroxide in ethanol followed by neutralisation with acid.
(c) an alkoxycarbonyl group may be converted to $CONR_{10}R_{11}$ by heating with the appropriate amine;
(d) a nitro group may be converted to an amino group by reduction, preferably by catalytic reduction using palladium on charcoal;
(e) an amino group may be converted to an alkylamino or acylamino group by conventional amine acylation or alkylation; the acylation is preferably carried out using an acid anhydride and the alkylation using the alkyl halide;
(f) an amino group may be converted to an alkylsulphonyl group by reaction with the appropriate alkylsulphonyl chloride, preferably using an acid acceptor such as triethylamine in an inert solvent such as dichloromethane.

An $R_4$ hydrogen atom may be converted to an $R_4$ $C_{1-6}$ alkyl group by conventional alkylation procedures.

It will be appreciated that these conversions may take place in any desired or necessary order. Conversions involving amine substitution may also substitute an $R_4$ hydrogen which therefore may need to be protected using an amine protecting group.

Pharmaceutically acceptable salts of the compounds of formula (I) may be formed conventionally by reaction with the appropriate acid.

Compounds of the formula (IX) are either known compounds or can be prepared by analogy with processes for preparing structurally similar known compounds.

For example, compounds of the formula (IX) wherein Q is chloro may be prepared by the phosphorus oxychloride chlorination of a compound of formula (XI):

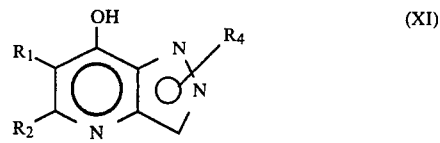

Compounds of the formula (X) may be prepared as described in J. Chem. Soc. Perkin Trans. I, 1976 (5), 507 or by analogous methods thereto.

It will be appreciated that the compounds of formula (XI) wherein $R_4$ is hydrogen exist in the predominant tautomeric form of formula (XIa):

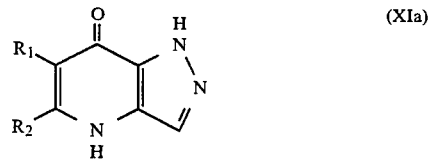

In a further aspect the invention provides a pharmaceutical composition which comprises a compound of formula (I) or a pharmaceutically acceptable salt thereof and a pharmaceutically acceptable carrier. The compositions may be adapted for administration via the topical, oral, rectal or injection routes. The compositions of this invention may contain diluents, binders, fillers, disintegrants, flavouring agents, colouring agents, lubricants, preservatives in conventional manner. These conventional excipients may be employed in conventional manner, for example as in the preparation of compositions of ketoprofen, indomethacin, naproxen, acetylsalicyclic acid or other anti-inflammatory agents.

The compounds of the invention have topical anti-inflammatory activity and therefore will normally be made up into a cream, lotion, gel or ointment for topical administration to the skin comprising a compound of the formula (I) which has been formulated as a cream, lotion, gel or ointment.

Cream, lotion, gel or ointment formulations that may be used for compounds of the formula (I) are conventional formulations well known in the art, for example, as described in standard text books of pharmaceutics and cosmetics, such as Harry's Cosmeticology published by Leonard Hill Books, and the British Pharmacopoeia. A standard emulsifying ointment base or anhydrous polyethylene glycol are simple examples of such suitable formulations.

Examples of oils suitable for inclusion in a standard emulsifying ointment base include mineral oils, vegetable oils, synthetic fatty acid esters, fatty alcohols, lanolin and its derivatives.

These compositions will normally include a suitable emulsifier. The composition can range from liquid through semi-liquid to gel types according to the type of emulsion and quantity of any thickening agent which may be present. Examples of emulsifiers include polyhydric alcohol esters such as sorbitan monostearate, fatty acid esters such as glyceryl monostearate, and polyester derivatives of fatty acids or fatty alcohols.

The compositions may also contain anti-oxidants and other conventional ingredients such as preservatives, perfumes and alcohol. Advantageously, a penetrating agent such as AZONE may also be included.

The compositions for topical treatment may also contain other thereapeuitic agents such as anti-infective and/or anti-viral agents. Suitable anti-infective agents include the topically applicable antibacterial, anti-yeast, anti-fungal and anti-herpes agents.

These compositions may be used in the topical treatment of atopic and contact dermatitis, psoriases, acne, eczeme and other inflammatory dermatoses and inflammatory conditions of eyes, ears, nose and throat. Treatment of inflammation of the skin may, however, also be carried out utilising an oral composition of the invention, as hereinbefore described.

It will be appreciated that the amount of compound of the formula (I) used will depend on a number of factors such as the nature and severity of the disorder being treated, and the specific compound being used. However, by way of illustration it is believed that effective therapy can be achieved using roughly similar amounts of the compounds of formula (I) as would be used of hydrocortisone. A typical formulation will suitably contain 0.1 to 20%, more suitably 0.5 to 5% of the compound of formula (I).

A composition of this invention is useful in the treatment of rheumatism and arthritis and in the treatment of pain and other inflammatory conditions and also in the treatment of the propylaxis of bronchial asthma, rhinitis, hay fever and allergic eczema. Suitably the oral compositions of this invention will be in the form of a unit dose such as a tablet, capsule or reconstitutable powder in a sachet. Such unit doses will generally contain from 10 mg to 1000 mg and more suitably will contain from about 30 mg to 500 mg for example 50 mg to 250 mg of active agent, for example about 50, 100, 150, 200, 250, 300, 350, 400, 450 or 500 mg. These compositions may be administered once or more times a day, for example 2, 3 or 4 times daily, so that the total daily dose for a 70 kg adult will usually be in the range of 20 to 3000 mg and more usually in the range 40 to 1000 mg. Alternatively the unit dose may contain from 2-20 mg of active agent and may be administered in multiples if desired to give the preceeding daily dose.

For use in the treatment or prophylaxis of allergic disorders, in any of the preceding formulations, a suitable dosage unit may contain 0.01 to 500 mg of active ingredient, more suitably 1 to 500 mg for use via the orgal route, 0.01 to 10 mg via inhalation, which is preferred. The effective dose of compound depends on the particular compound employed, the condition of the patient and the frequency and route of administration, but in general is in the range of from 0.001 mg/day to 100 mg/day per kilogram of the patient's body weight. No adverse toxicological effects are indicated at any of the aforementioned dosage ranges.

Where appropriate, small amounts of other anti-asthmatics and bronchodilators, for example sympathomimetic amines such as isoprenaline, isoetharine, slabutamol, phenylephrine and ephedrine; xanthine derivatives such as theophylline and aminophylline and corticosteroids such as prednisolone and adrenal stimulants such as ACTH may be included.

A favoured form of oral composition of this invention is a tablet containing the active agent. The active agent may be in the form of a recompressed granulate of the active ingredient in intimate mixture with a lubricant such as magnesium stearate, a filler such as microcrystalline cellulose and a disintegrant such as sodium starch glycollate.

A particular composition of the invention for inflammatory diseases is a hard gelatin capsule containing the required amount of a compound of the invention in the form of a powder or granulate in intimate mixture with a lubricant, such as magnesium stearate, a filler, such as microcrystalline cellulose, and a disintegrant, such as sodium starch glycollate.

Preparations especially suitable for administration to the respiratory tract include, for example, a snuff, an aerosol, a solution for a nebulizer, or a microfine powder for insufflation, alone or in combination with an inert carrier such as lactose. In such a case the particles of active compound suitably have diameters of less than 50 microns, preferably less than 10 microns. For parenteral administration, fluid unit dosage forms are prepared utilising a compound of the formula (I) or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. Parenteral suspensions are prepared in substantially the same manner, except that the compound is suspended in the vehicle instead of being dissolved and sterilised by exposure to ethylene oxide before suspension in a sterile vehicle. Advantageously, a surfactant or wetting agent is included in the composition to facilitate uniform distribution of the compound.

The invention further provides a method of treatment or prophylaxis of inflammatory and/or allergic conditions in mammals including man which comprises the administration of a compound of formula (I) or a pharmaceutically acceptable salt thereof to the sufferer.

The invention also provides a compound of formula (I) or a pharmaceutically acceptable salt thereof for use in treating inflammatory and/or allergic conditions in mammals.

Mmammals which may be thus treated include humans and domestic animals such as dogs, cats or horses.

Most suitably the medicament will be administered orally as 1, 3 or 4 doses per day at the dose level previously indicated.

The following Examples illustrate the invention and the following Descriptions illustrate the preparation of intermediate thereto.

DESCRIPTION 1

Ethyl 7-chloro-1H-pyrazolo[4,3-b]pyridine-6-carboxylate

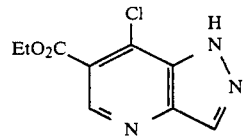

A solution of ethyl 4,7-dihydro-7-oxo-1H-pyrazolo[4,3-b]pyridine-6-carboxylate[1] in phosphorus oxychloride was heated under reflux for 45 min. After removing excess reagent in vacuo, the residue was made basic with saturated sodium hydrogen carbonate solution. The precipitated solid was washed with water, then extracted with ethyl acetate to give the crude title compound.

1. H. E. Foster and J. Hurst, J. Chem. Soc., Perkin Trans. 1, 1976, 507

δ (DMSO d6) 1.4 (3H, t, J=7 Hz), 4.3 (2H, q, J=7 Hz), 8.4 (1H, s), 8.8 (1H, s).

A much improved yield (67%) of the title compound was obtained by maintaining the reaction mixture at 70°–80° C. rather than at reflux temperature.

DESCRIPTION 2

Diethyl 2-(Pyrazol-4-ylamino)fumarate

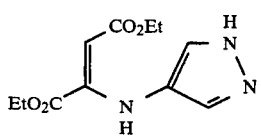

A solution of 4-nitropyrazole (8.4 g, 75 mmol) in ethanol (300 ml) was hydrogenated over 10% palladium on charcoal (800 mg) for 3.5 h. The mixture was filtered and cooled to 5° C. Diethyl acetylenedicarboxylate (12 ml, 75 mmol) was added dropwise with stirring over 10 min. The solvent was removed in vacuo, and column chromatography (SiO2, 2% methanol/ether) gave the fumarate which was crystallised from ether/pentane to give the title compound as plates (8.22 g, 43%), m.p. 69°–71° C.

Found: C, 52.16; H, 6.00; N, 16.46. $C_{11}H_{15}N_3O_4$ requires C, 52.17; H, 5.97; N, 16.59%.

δ (CDCl3) : 1.15 (3H, t, J=7 Hz), 1.30 (3H, t, J=7 Hz), 4.15 (2H, q, J=7 Hz), 4.22 (2H, q, J=7 Hz), 5.25 (1H, s), 7.45 (2H, s), 8.00 (1H, bs), 9.25 (1H, bs).

DESCRIPTION 3

Ethyl 4,7-dihydro-7-oxo-1H-pyrazolo[4,3-b]pyridine-5-carboxylate

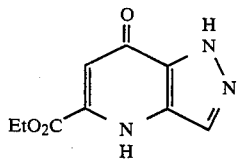

Diethyl 2-(pyrazol-4-ylamino)fumarate (7.74 g, 30 mmol) was added to boiling Dowtherm A (250 ml). The solution was heated under reflux for 10 min, and then allowed to cool to room temperature. 60°–80° petrol (250 ml) added and the solid was collected and washed well with petrol, to give the title compound as pale yellow needles (5.77 g, 99%), m.p. 287°–292° C.

δ (TFAD): 1.60 (3H, t, J=7 Hz), 4.80 (2H, q, J=7 Hz), 8.10 (1H, s), 8.80 (2H, s).

Found: C, 52.02; H, 4.41; N, 20.18. $C_9H_9N_3O_3$ requires: C, 52.17; H, 4.38; N, 20.28.

DESCRIPTION 4

Ethyl 7-chloro-1H-pyrazolo[4,3-b]pyridine-5-carboxylate

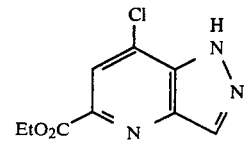

Ethyl 4,7-dihydro-7-oxo-1H-pyrazolo[4,3-b]pyridine-5-carboxylate (5.0 g, 24 mmol) was heated under reflux in phosphoryl chloride (50 ml) for 25 min. Excess reagent was removed in vacuo and the residue was treated with water to give a yellow solid. After neutralisation with 10% sodium hydroxide solution, the solid was collected and dried to give the title compound (4.48 g, 83%), m.p. 276°–279° C. after recrystallisation from ethyl acetate.

δ (DMSO-d6): 1.40 (3H, t, J=7 Hz), 4.40 (2H, q, J=7 Hz), 8.13 (1H, s), 8.67 (1H, s).

Found: C, 47.75; H, 3.32; N, 18.74; Cl, 15.78. $C_9H_8N_3O_2Cl$ requires: C, 47.91; H, 3.57; N, 18.62; Cl, 15.71.

DESCRIPTION 5

Ethyl 7-chloro-2-methyl-pyrazolo[4,3-b]pyridine-6-carboxylate

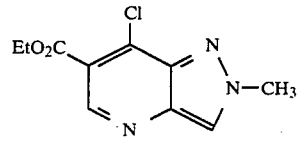 (D5)

Ethyl 7-chloro-1H pyrazolo[4,3-b]pyridine-6-carboxylate (4.5 g, 0.02 mole) and dimethyl formamide demethylacetal[2] (10 ml, 0.04 mole) in dry toluene (200 ml) were heated together under reflux for 1 h. The solvent and excess of reagent were distilled off under reduced pressure to give a brown oil containing two isomers. The 1-methyl[3] and 2-methyl isomers were separated by column chromatography on silica gel with ethyl acetate as eluant to give the title compound as a white crystalline solid m.p. 118°–120° C.

2. R. W. Middleton et al., Synthesis, (1984) 740

δ (CDCl3): 1.45 (3H, t, J=7 Hz), 4.25 (3H, s,), 4.35 (2H, q, J=7 Hz), 8.10 (1H, s), 8.75 (1H, s).

The physical characteristics of the isomeric 1-methyl compound were the same as the literature[3] values.

3. H. E. Foster and J. Hurst, J. C. S. Perkin I, (1976) 507

DESCRIPTION 6

7-Chloro-1H-5-trifluoromethylpyrazolo[4,3-b]pyridine (D6)

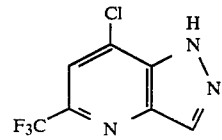 (D6)

The title compound was prepared by the method given in Description 1 as a pale yellow solid, m.p. 172°–180° C.

δ (DMSO-d₆) 8.12 (1H, s), 8.17 (1H, s).
Found M+ 220.9968. C₇H₃ClF₃N₃ 220.9967.

EXAMPLE 1

Ethyl 7-anilino-1H-pyrazolo[4,3-b]pyridine-6-carboxylate

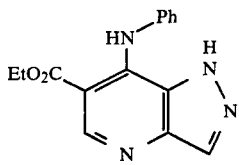

(I)

Ethyl 7-chloro-1H-pyrazolo[4,3-b]-pyridine-6-carboxylate (370 mg, 1.6 mmol) was dissolved in aniline (3 ml) and stirred overnight. The resulting mixture was triturated with 60°–80° petrol, and the precipitated solid was collected and dissolved in aqueous ethanol. The solution was adjusted to pH 8 with saturated sodium hydrogen carbonate solution, and the precipitated solid was collected to give the title compound (310 mg, 67%) m.p. 164°–165° C.

δ(DMSO d₆) 1.3 (3H, t, J=7 Hz), 4.25 (2H, q, J=7 Hz), 7.2 (5H, m), 8.2 (1H, s), 8.7 (1H, s), 10.1 (1H, br s).

EXAMPLE 2

Ethyl 7-Allylamino-1H-pyrazolo[4,3-b]-pyridine-6-carboxylate (E2).

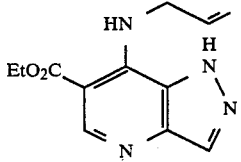

(E2)

Ethyl 7-chloro-1H-pyrazolo[4,3-b]pyridine-6-carboxylate (2.25 g, 0.01 mole) and allylamine (20 ml) were stirred together overnight at room temperature. The excess allylamine was removed under reduced pressure. The residue was dissolved in the minimum volume of aqueous ethanol and sufficient 10% sodium carbonate added to give pH 8.

The resulting solid was collected and dried to give a yellow solid, which was recrystallized from ether-pentane with a few drops of methanol to facilitate solubility, to give the title compound as the free base (1.0 g, 42%) m.p. 218°–222° C. (Found: C, 58.32; H, 5.72; N, 22.85. C₁₂H₁₄N₄O₂ requires C, 58.53; H, 5.73; N, 22.75%)

δ(CDCl₃) 1.4 (3H, t, J=7 Hz), 4.3 (2H, q, J=7 Hz), 4.7–4.85 (2H, m), 5.05–5.5 (2H, m), 5.75–6.41 (1H, m), 8.15 (1H, s), 8.8 (1H, s).

EXAMPLE 3

Ethyl 7-(4-Hydroxyanilino)-1H-pyrazolo[4,3-b]pyridine-6-carboxylate (E3)

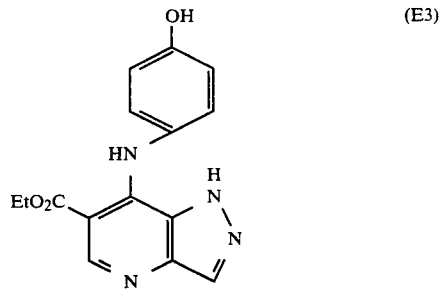

(E3)

Ethyl 7-chloro-1H pyrazolo[4,3-b]pyridine-6-carboxylate (1.0 g, 0.004 mole) and p-aminophenol (1.0 g, 0.009 mole) were stirred together in ethyl acetate (200 ml) under nitrogen for 48 hours, the temperature being maintained between −10° and −5° C. The ethyl acetate was removed under reduced pressure to give a yellow solid. This solid was dissolved in aqueous ethanol and the pH adjusted to pH8 with 10% sodium carbonate solution. The resulting solid was filtered off washed with water and dried. Recrystallization from methanol/ethyl acetate gave the title compound as a pale yellow solid (650 mg, 50%), m.p. 286°–287° C. (decomposition)

(Found: C, 60.28; H, 4.97; N, 18.70. C₁₅H₁₄N₄O₃ requires C, 60.40; H, 4.73; N, 18.78%).

δ (DMSO-d₆) 1.45 (3H, t, J=7 Hz), 4.3 (2H, q, J=7 Hz), 6.75 (2H, d, J=4 Hz), 7.11 (2H, d, J=4 Hz), 8.20 (1H, s), 8.71 (1H, s).

EXAMPLE 4

Ethyl 7-Amylamino-1H-pyrazolo[4,3-b]pyridine-6-carboxylate (E4)

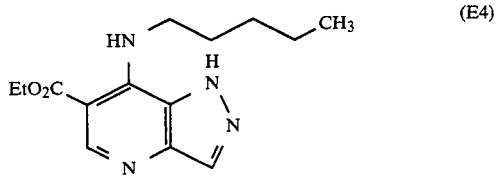

(E4)

The above compound was prepared from ethyl 7-chloro-1H-pyrazolo[4,3-b]pyridine-6-carboxylate and n-amylamine in an analogous manner to the preparation of Example 2 giving a pale yellow solid, m.p. 153°–155° C.

δ(CDCl₃) 0.7–1.8 (6H, m), 1.4 (2H, t, J=7 Hz), 1.9 (3H, s), 3.7–4.0 (2H, m), 4.3 (2H, q, J=7 Hz), 8.0 (1H, s), 8.75 (1H, s).

EXAMPLE 5

Ethyl 7-Phenylthio-1H-pyrazolo[4,3-b]pyridine-6-carboxylate (E5)

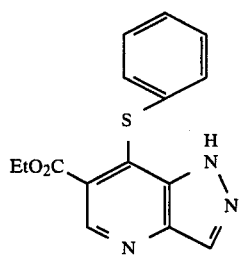
(E5)

The above compound was prepared from ethyl 7-chloro-1H-pyrazolo[4,3-b]pyridine-6-carboxylate and thiophenol in an analogous manner to the preparation of Example 1 giving a white solid, m.p. 130°–131° C.

Found: C, 60.09; H, 4.52; N, 13.96; $C_{15}H_{13}N_3SO_2$ requires C, 60.18; H, 4.38; N, 14.04%).

δ (CDCl$_3$) 1.48 (3H, t, J=7 Hz), 4.5 (2H, q, J=7 Hz), 7.35–7.85 (5H m,), 8.28 (1H, s), 9.05 (1H, s).

EXAMPLE 6

Ethyl 7-n-Butylamino-1H-pyrazolo[4,3-b]pyridine-6-carbosylate (E6)

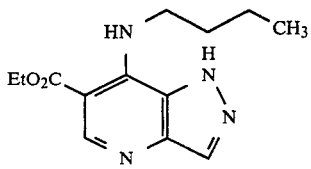
(E6)

Ethyl 7-chloro-1H-pyrazolo[4,3-b]pyridine-6-carboxylate (3.5 g, 15.5 mmol) was dissolved in n-butylamine (25 ml) and stirred at room temperature for 3 h. Excess butylamine was removed in vacuo and the residual solid was washed well with water, and recrystallised from ethyl acetate to give the title compound (2.75 g, 67%), m.p. 164°–170° C.

Found: C, 59.04; H, 6.91; N, 21.19; $C_{13}H_{18}N_4O_2$ requires C, 59.53; H, 6.92; N, 21.36.

δ (DMSO-d6) 0.95 (3H, t, J=7 Hz), 1.35 (3H, t, J=7 Hz), 1.2–1.8 (4H, m), 4.05 (2H, m), 4.35 (2H, q, J=7 Hz), 8.35 (1H, s), 8.70 (1H, s), 9.10 (1H, t, exchanged with D$_2$O).

EXAMPLE 7

7-Allylamino-1H-pyrazolo[4,3-b]pyridine-5-carboxylic acid allyl amide (E7)

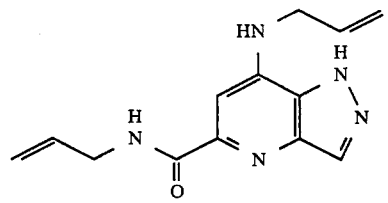
(E7)

A solution of ethyl 7chloro-1H-pyrazolo[4,3-b]-pyridine-5-carboxylate (1.5 g, 6.65 mmol) in allylamine (25 ml) was heated under reflux for 3 days. The solvent was evaporated in vacuo and the residue was extracted into warm ether to give 7-chloro-1H-pyrazolo[4,3-b]pyridine-5-carboxylic acid allyl amide as a pale yellow solid, m.p. 121°–125° C. Without further purification, this material was dissolved in allylamine (10 ml) and water (10 ml) and heated under reflux for 6 days. Excess allylamine was removed in vacuo and the precipitated solid was collected and washed well with water, to give the crude product (940 mg, 55%). Recrystallisation from ethyl acetate gave the title compound, m.p. 194°–197° C.

δ(DMSOd$_6$): 3.85 (2H, t), 4.12 (2H, t), 4.95–5.45 (4H, m), 5.50–6.20 (5H, m), 7.25 (1H, s), 8.17 (1H, s), 8.40 (1H, t, exchanged with D$_2$O).

EXAMPLE 8

Ethyl 7-Allylamino-1H-pyrazolo[4,3-b]pyridine-5-carboxylate (E8)

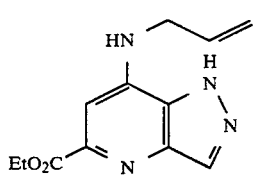
(E8)

A suspension of 7-allylamino-1H-pyrazolo[4,3-b]-pyridine-5-carboxylic acid allylamide (500 mg, 1.94 mmol) in ethanolic hydrogen chloride (15 ml) was heated under reflux for 5 days with periodic addition of small aliquots of ethanolic hydrogen chloride. The solvent was evaporated in vacuo and the residue was dissolved in warm aqueous ethanol. The solution was adjusted to pH 8 with aqueous sodium carbonate solution, and after evaporation of excess ethanol, the product (170 mg, 37%) was collected and washed well with water. Recrystallisation from ethanol/ether gave the title compound, m.p. 140°–145° C.

δ(DMSO-d$_6$): 1.35 (3H, t, J=7 Hz), 4.05 (2H, m), 4.35 (2H, q, J=7 Hz), 5.00–5.50 (2H, m), 5.57–6.30 (1H, m), 7.05 (1H, s), 7.05 (1H, bs, exchanged with D$_2$O), 8.30 (1H, s), 13.00 (1H, bs, exchanged with D$_2$O).

EXAMPLE 9

7-Anilino-1H-pyrazolo[4,3-b]pyridine-5-carboxylic acid anilide (E9)

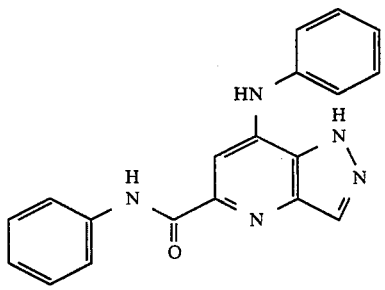
(E9)

A solution of ethyl 7-chloro-1H-pyrazolo [4,3-b]-pyridine-5-carboxylate (1.2 g, 5.3 mmol) in aniline (10 ml) was heated under reflux under nitrogen for 24 h. The mixture was cooled, diluted with ethyl acetate, and the precipitated product was collected. Column chromatography on silica, eluting with 5% methanol/ethyl acetate gave the title compound which was recrystallised from ethyl acetate to give a white solid (0.57 g, 33%) mp 248°–250° C.

δ (DMSO-d$_6$) 6.95–7.6 (9H, m), 7.70 (1H, s), 7.85 (2H, dd, J=7, 2 Hz), 8.35 (1H, s), 8.90 (1H, br s, exchanges with D$_2$O), 10.50 (1H, br s, exchanges with D$_2$O).

EXAMPLE 10

Ethyl 7-Anilino-1H-pyrazolo[4,3-b]pyridine-5-carboxylate (E10)

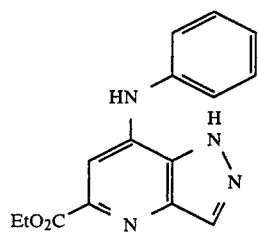

The title compound was prepared by the method of Example 8 as a pale yellow solid (47%) mp. 230°–234° C.

δ (DMSO d$_6$) 1.30 (3H, t, J=7 Hz), 4.30 (2H, q, J=7 Hz), 7.0–7.55 (5H, m), 7.60 (1H, s), 8.40 (1H, s), 8.93 (1H, s, exchanges with D$_2$O), 12.90 (1H, br s, exchanges with D$_2$O).

EXAMPLE 11

Ethyl 7-allylamino-2-methyl-pyrazolo[4,3-b]pyridine-6-carboxylate (E11)

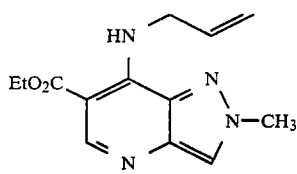

The above compound was prepared from ethyl 7-chloro-2-methyl-pyrazolo[4,3-b]pyridine and n-allylamine in an analogous manner to the preparation of Example 2 to give a white solid, m.p. 140°–143° C.

δ (CDCl$_3$) 1.39 (3H, t, J=7 Hz), 4.10 (3H, s), 4.28 (2H, q, J=7 Hz), 4.6–5.45 (4H, m), 5.75–6.45 (1H, m), 7.80 (1H, s), 8.70 (1H, s).

EXAMPLE 12

7-Isobutylamino-1H-5-trifluoromethylpyrazolo-[4,3-b]pyridine (E12)

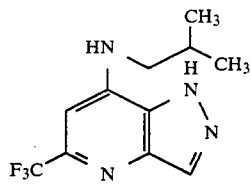

7-Chloro-1H-5-trifluoromethylpyrazolo[4,3-b]pyridine (D6) (0.24 g) in iso-butylamine (5 ml) was heated at reflux for 2 days and then evaporated to dryness. The residue was chromatographed on silica gel with ether as eluant to give a white crystalline solid. The solid was taken up in a small volume of methanol and water added. The solution was brought to pH 8 with aqueous ammonia. The resulting white solid, the required free base, was collected, washed with water and dried, m.p. 194°–196° C.

(Found: C, 51.14; H, 5.20; N, 21.91. C$_{11}$H$_{13}$F$_3$N$_4$ requires C, 51.16; H, 5.06; N, 21.70%)

δ (DMSO-d$_6$) 1.01 (6H, d, J=6 Hz), 1.6–2.3 (1H, m), 3.05–3.35 (2H, m), 6.67 (1H, s), 6.94 (1H, br.t, exchanges with D$_2$O), 8.25 (1H, s), 13.05 (1H, br.s, exchanges with D$_2$O).

Found M+ 258.1089. C$_{11}$H$_{13}$F$_3$N$_4$ requires 258.1092.

PHARMACOLOGICAL DATA

Mouse Oxazolone Screen

Compounds were tested for topical anti-inflammatory activity in a screen using the mouse sensitised to oxazolone, by a method modified from that of Dietrich and Hess [Dietrich, F. M., and Hess, R., Int. Arch. Allergy, (1970), 38, 246–259].

Mice were sensitised with oxazolone (2 mg in 20 μl ethanol) on a shaved area of the abdomen. Five days later, the animals recieved 10 μl THF/MeOH (1:1 v/v) on the right ear, and the test compound in the same solvent on the left ear. One hour later, the animals were challenged with 100 μg oxazolone in 10 μl acetone on each ear. Ear weights were measured 24 h later. Percentage inhibition of the inflammatory swelling refers to the increase in weight of left ears (oxazolone plus compound) compared with solvent-treated negative controls, as a proportion of the increase in weight of right ears (oxazolone alone) over similar controls.

In this test the compound of Example 1 had an inhibition of 24% at a dose of 500 μg/ear.

Mouse Cantharidin Screen

Compounds were tested for topical anti-inflammatory activity in a cantharidin mouse ear screen, modified from Swinge et al [Swingle, K. F., Reiter, M. J. and Schwartzmiller, D. H., Arch. Int. Pharmacodyn., (1981), 254, 168–176].

25 μg cantharidin (in 10 μl THF/MeOH) was applied to both ears. Compound, in the same solvent, was applied at the same time, to the left ear only. Ears were weight 24 h after cantharidin application. Percentage inhibition of the acute inflammatory swelling refers to the increase in weight of left ears (cantharidin plug compound) compared with solvent-treated negative controls, as a proportion of the increase in weight of right ears (cantharidin alone) over similar controls.

In this test the compound of Example 6 gave an inhibition of 42% at 200 μg/ear and the compound of Example 2 gave an inhibition of 20% at a dose of 500 μg/ear.

RBL-1 5-Lipoxygenase Screen

5-Lipoxygenase enzyme was prepared as a 10,000 g supernatant from RBL-1 cells by the method of Jakschik [Jakschik, B. A., Sun. F. F., Lee, L. M. and Steinhoff, M. M., 1980, Biochem. Biophys. Res. Comm. 95, 103]. The 10,000 g supernatant was diluted with homogenization buffer to the equivalent of 1.5–2.5×10$^7$ cells ml$^{-1}$ and made 2 mM with respect to CaCl$_2$. Aliquots of 0.5 ml were then dispensed into tubes, and incubated at 29° C. with 5 γl ethanol or compound in ethanol at the desired concentration for 2 min. Then [1-$^{14}$C] arachidonic acid was added in buffer to give a final concentration of 6.3 μm and 0.2 μCi per incubation, and the reaction continued at 29° C. for 2 min. The reaction was terminated by adding 1 ml of acetone and cooling on ice, 0.5 ml of ice-cold saline and 10 μl of 2N formic acid were added, and the mixture was extracted with 2×2 ml of chloroform. The extract was stored under $N_2$ at −20° C. until analysis by chromatography. Activity was measured as the percentage of total radioactivity found in 5-HETE and 5,12-diHETE, and inhibition calculated as the decrease in formation of the sum of these two species in compound-treated incubates relative to control incubates.

In this test the compound of Exampble 6 gave an inhibition of 78% at 20 μM.

We claim:

1. A compound of formula (I) or a pharmaceutically acceptable salt thereof:

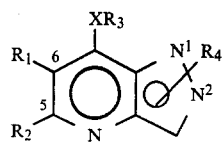

wherein:

X is sulphur SO or NR wherein R is hydrogen of $C_{1-6}$ alkyl, $SO_2$;

$R_1$ is $COR_5$ wherein $R_5$ is hydroxy, $C_{1-6}$ alkoxy, $C_{2-6}$ alkenyloxy, phenoxy or benzyloxy wherein the phenyl and benzyl moieties are optionally substituted by one or two of halogen, $CF_3$, $C_{1-4}$ alkoxy and $C_{1-4}$ alkyl; or $R_5$ is $NR_{13}R_{14}$ wherein $R_{13}$ and $R_{14}$ are independently hydrogen, $C_{2-6}$ alkyl, $C_{2-6}$ alkenyl, benzyl or phenyl wherein the phenyl and benzyl moieties are optionally substituted by one or two of halogen, $CF_3$, $C_{1-4}$ alkoxy and $C_{1-4}$ alkyl; or $CF_3$; and $R_2$ is hydrogen, $C_{1-6}$ alkyl or phenyl optionally substituted by halogen, $CF_3$, $C_{1-4}$ alkoxy or $C_{1-4}$ alkyl; or $R_2$ is $COR_5$ as defined above or $CF_3$ and $R_1$ is hydrogen;

$R_3$ is $C_{1-10}$ alkyl, optionally substituted by hydroxy, $C_{1-4}$ alkoxy, thiol, $C_{1-4}$ alkylthio or $NR_6R_7$ wherein $R_6$ and $R_7$ are independently hydrogen or $C_{1-6}$ alkyl or together are $C_{3-6}$ polymethylene; $C_{2-10}$ alkenyl or phenyl optionally substituted by one or two halogen, $CF_3$, $C_{1-4}$ alkoxy, $C_{1-4}$ alkyl, hydroxy, nitro, cyano, $C_{2-10}$ carboxylic acyloxy, $NR_8R_9$ wherein $R_8$ and $R_9$ are independently selected from hydrogen, $C_{1-6}$ alkyl, $C_{2-7}$ alkanoyl or $C_{1-6}$ alkylsulphonyl or $COR_{10}$ wherein $R_{10}$ is hydroxy, $C_{1-6}$ alkoxy or $NR_{11}R_{12}$ wherein $R_{11}$ and $R_{12}$ are independently selected from hydrogen or $C_{1-6}$ alkyl; and $R_4$ is hydrogen; or $C_{1-4}$ alkyl or benzyl attached at nitrogen atom 1 or 2.

2. A compound according to claim 1 of formula (III):

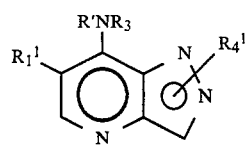

wherein $R_1{}^1$ is $COR_5{}^1$, wherein $R_5{}^1$ is hydroxy $C_{1-6}$ alkoxy, $C_{2-6}$ alkenyloxy, phenoxy or benzyloxy wherein the phenyl and benzyl moieties are optionally substituted by one or two of halogen, $CF_3$, $C_{1-4}$ alkoxy and $C_{1-4}$ alkyl; or $R_5{}^1$ is $NR_{13}R_{14}$ wherein $R_{13}$ and $R_{14}$ are independently hydrogen, $C_{2-6}$ alkyl, $C_{2-6}$ alkenyl, benzyl or phenyl wherein the phenyl and benzyl moieties are optionally substituted by one or two of halogen, $CF_3$, $C_{1-4}$ alkoxy and $C_{1-4}$ alkyl; or $R_1{}^1$ is $CF_3$, R' is hydrogen or methyl, $R_4{}^1$ is hydrogen or 2-methyl, and $R_3$ is as defined in claim 1.

3. A compound according to claim 2 of formula (IV):

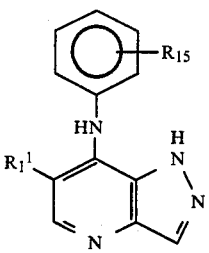

wherein $R_{15}$ is hydrogen, chloro, bromo, methoxy, ethoxy, hydroxy, cyano, carboxyl, ethoxycarbonyl, nitro or t-butyl.

4. A compound according to claim 2 of formula (V):

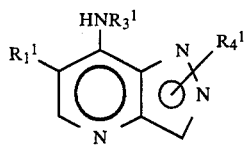

wherein $R_3{}^1$ is n-butyl, n-pentyl, allyl, 2-methylallyl, 2-hydroxyethyl, 3-hydroxypropyl, 2-thiolethyl, 2-methoxyethyl, 2-dimethylaminoethyl, 3-dimethylaminopropyl, 2-pyrrolidinoethyl 3-pyrrolidinopropyl and $R_1{}^1$ and $R_4{}^1$ are as defined in claim 2.

5. A compound according to claim 1 of formula (VI):

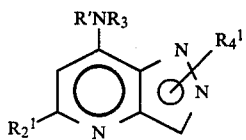

wherein $R_2{}^1$ is $COR_5{}^1$ wherein $R_5{}^1$ is hydroxy, $C_{1-6}$ alkoxy, $C_{2-6}$ alkenyloxy, phenoxy or benzyloxy wherein the phenyl and benzyl moieties are optionally substituted by one or two of halogen, $CF_3$, $C_{1-4}$ alkoxy and $C_{1-4}$ alkyl; or $R_5{}^1$ is $NR_{13}R_{14}$ wherein $R_{13}$ and $R_{14}$ are independently hydrogen, $C_{2-6}$ alkyl, $C_{2-6}$ alkenyl, benzyl or phenyl wherein the phenyl and benzyl moieties are optionally substituted by one or two of halogen, $CF_3$, $C_{1-4}$ alkoxy and $C_{1-4}$ alkyl;

R' is hydrogen or methyl;

$R_4{}^1$ is hydrogen or 2-methyl; and $R_3$ is $C_{1-10}$ alkyl, optionally substituted by hydroxy, $C_{1-4}$ alkoxy, thiol, $C_{1-4}$ alkylthio or $NR_6R_7$ wherein $R_6$ and $R_7$ are independently hydrogen or $C_{1-6}$ alkyl or together are $C_{3-6}$ polymethylene; $C_{2-10}$ alkenyl or phenyl optionally substituted by one or two of halogen, $CF_3$, $C_{1-4}$ alkoxy, $C_{1-4}$ alkyl, hydroxy, nitro, cyano, $C_{2-10}$ carboxylic acyloxy, $NR_8R_9$ wherein $R_8$ and $R_9$ are independently selected from hydrogen, $C_{1-6}$ alkyl, $C_{2-7}$ alkanoyl or $C_{1-6}$ alkylsulphonyl or $COR_{10}$ wherein $R_{10}$ is hydroxy, $C_{1-6}$ alkoxy or $NR_{11}R_{12}$ wherein $R_{11}$ and $R_{12}$ are independently selected from hydrogen or $C_{1-6}$ alkyl.

6. A compound according to claim 5 of formula (VII):

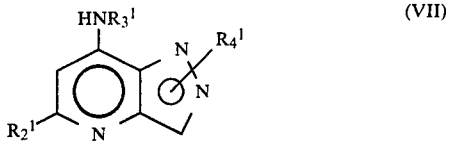

wherein $R_3^1$ is n-butyl, n-pentyl, allyl, 2-methylallyl, 2-hydroxyethyl, 3-hydroxypropyl, 2-thioethyl, 2-methoxyethyl, 2-dimethylaminoethyl, 3-dimethylaminopropyl, 2-pyrrolidinoethyl, or 3-pyrrolidinopropyl and $R_4^1$ is hydrogen or 2-methyl and $R_2^1$ is $COR_5^1$ wherein $R_5^1$ is hydroxy, $C_{1-6}$ alkoxy, $C_{2-6}$ alkenyloxy, phenoxy or benzyloxy wherein the phenyl and benzyl moieties are optionally substituted by one or two of halogen, $CF_3$, $C_{1-4}$ alkoxy and $C_{1-4}$ alkyl; or $R_5^1$ is $NR_{13}R_{14}$ wherein $R_{13}$ and $R_{14}$ are independently hydrogen, $C_{2-6}$ alkyl, $C_{2-6}$ alkenyl, benzyl or phenyl wherein the phenyl and benzyl moieties are optionally substituted by one or two of halogen, $CF_3$, $C_{1-4}$ alkoxy and $C_{1-4}$ alkyl.

7. A compound selected from the group consisting of ethyl 7-anilino-1H-pyrazolo[4,3-b]pyridine-6-carboxylate,
ethyl 7-Allylamino-1H-pyrazolo[4,3-b]-pyridine-6-carboxylate,
ethyl 7-(4-Hydroxyanilino)-1H-pyrazolo[4,3-b]pyridine-6-carboxylate,
ethyl 7-Amylamino-1H-pyrazolo[4,3-b]pyridine-6-carboxylate,
ethyl 7-Phenylthio-1H-pyrazolo[4,3-b]pyridine-6-carboxylate,
ethyl 7-n-Butylamino-1H-pyrazolo[4,3-b]pyridine-6-carboxylate, 7-allylamino-1H-pyrazolo[4,3-b]pyridine-5-carboxylic acid allyl amide,
ethyl 7-Allylamino-1H-pyrazolo[4,3-b]pyridine-5-carboxylate,
7-anilino-1H-pyrazolo[4,3-b]pyridine-5-carboxylic acid anilide,
ethyl 7-Aniliono-1H-pyrazolo[4,3-b]pyridine-5- carboxylate,
ethyl 7-allylamino-2-methyl-pyrazolo [4,3-b]pyridine-6-carboxylate and
7-isobutylamino-1H-5-trifluoromethylpyrazolo-[4,3-b]pyridine.

8. A pharmaceutical composition for the treatment of inflammatory or allergic conditions comprising an effective amount of a compound of formula (I):

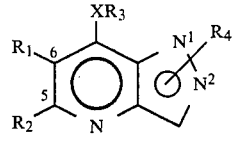

wherein:
X is oxygen, sulphur, SO or $SO_2$ or NR wherein R is hydrogen or $C_{1-6}$ alkyl;
$R_1$ is $COR_5$ wherein $R_5$ is hydroxy, $C_{1-6}$ alkoxy, $C_{2-6}$ alkenyloxy, phenoxy or benzyloxy wherein the phenyl and benzyl moieties are optionally substituted by one or two of halogen, $CF_3$, $C_{1-4}$ alkoxy and $C_{1-4}$ alkyl; or $R_5$ is $NR_{13}R_{14}$ wherein $R_{13}$ and $R_{14}$ are independently hydrogen, $C_{2-6}$ alkyl, $C_{2-6}$ alkenyl, benzyl or phenyl wherein the phenyl and benzyl moieties are optionally substituted by one or two of halogen, $CF_3$, $C_{1-4}$ alkoxy and $C_{1-4}$ alkyl; or $CF_3$; and $R_2$ is hydrogen, $C_{1-6}$ alkyl or phenyl optionally substituted by halogen, $CF_3$, $C_{1-4}$ alkoxy or $C_{1-4}$ alkyl; or $R_2$ is $COR_5$ as defined above or $CF_3$ and $R_1$ is hydrogen;
$R_3$ is $C_{1-10}$ alkyl, optionally substituted by hydroxy, $C_{1-4}$ alkoxy, thiol, $C_{1-4}$ alkylthio or $NR_6R_7$ wherein $R_6$ and $R_7$ are independently hydrogen or $C_{1-6}$ alkyl or together are $C_{3-6}$ polymethylene; $C_{2-10}$ alkenyl or phenyl optionally substituted by one or two halogen, $CF_3$, $C_{1-4}$ alkoxy, $C_{1-4}$ alkyl, hydroxy, nitro, cyano, $C_{2-10}$ carboxylic acyloxy, $NR_8R_9$ wherein $R_8$ and $R_9$ are independently selected from hydrogen, $C_{1-6}$ alkyl, $C_{2-7}$ alkanoyl or $C_{1-6}$ alkylsulphonyl or $COR_{10}$ wherein $R_{10}$ is hydroxy, $C_{1-6}$ or $NR_{11}R_{12}$ wherein $R_{11}$ and $R_{12}$ are independently selected from hydrogen or $C_{1-6}$ alkyl; and $R_4$ is hydrogen; or $C_{1-4}$ alkyl or benzyl attached at nitrogen atom 1 or 2;
or a pharmaceutically acceptable salt thereof and a pharmaceutically acceptable carrier.

9. A method of treatment of inflammatory or allergic conditions in mammals comprising the adminstration of an effective amount of a compound of formula I:

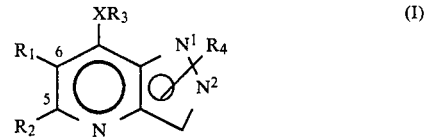

wherein:
X is oxygen, sulphur, SO or $SO_2$ or NR wherein R is hydrogen or $C_{1-6}$ alkyl;
$R_1$ is $COR_5$ wherein $R_5$ is hydroxy, $C_{1-6}$ alkoxy, $C_{2-6}$ alkenyloxy, phenoxy or benzyloxy wherein the phenyl and benzyl moieties are optionally substituted by one or two of halogen, $CF_3$, $C_{1-4}$ alkoxy and $C_{1-4}$ alkyl; or $R_5$ is $NR_{13}R_{14}$ wherein $R_{13}$ and $R_{14}$ are independently hydrogen, $C_{2-6}$ alkyl, $C_{2-6}$ alkenyl, benzyl or phenyl wherein the phenyl and benzyl moieties are optionally substituted by one or two of halogen, $CF_3$, $C_{1-4}$ alkoxy and $C_{1-4}$ alkyl; or $CF_3$; and $R_2$ is hydrogen, $C_{1-6}$ alkyl or phenyl optionally substituted by halogen, $CF_3$, $C_{1-4}$ alkoxy or $C_{1-4}$ alkyl; or $R_2$ is $COR_5$ as defined above or $CF_3$ and $R_1$ is hydrogen;
$R_3$ is $C_{1-10}$ alkyl, optionally substituted by hydroxy, $C_{1-4}$ alkoxy, thiol, $C_{1-4}$ alkylthio or $NR_6R_7$ wherein $R_6$ and $R_7$ are independently hydrogen or $C_{1-6}$ alkyl or together are $C_{3-6}$ polymethylene; $C_{2-10}$ alkenyl or phenyl optionally substituted by one or two halogen, $CF_3$, $C_{1-4}$ alkoxy, $C_{1-4}$ alkyl, hydroxy, nitro, cyano, $C_{2-10}$ carboxylic acyloxy, $NR_8R_9$ wherein $R_8$ and $R_9$ are independently selected from hydrogen, $C_{1-6}$ alkyl, $C_{2-7}$ alkanoyl or $C_{1-6}$ alkylsulphonyl or $COR_{10}$ wherein $R_{10}$ is hydroxy, $C_{1-6}$ alkoxy or $NR_{11}R_{12}$ wherein $R_{11}$ and $R_{12}$ are independently selected from hydrogen or $C_{1-6}$ alkyl; and $R_4$ is hydrogen; or $C_{1-4}$ alkyl or benzyl attached at nitrogen atom 1 or 2;
or a pharmaceutically acceptable salt thereof to the sufferer.

* * * * *

UNITED STATES PATENT AND TRADEMARK OFFICE
CERTIFICATE OF CORRECTION

PATENT NO. : 4,621,089

DATED : November 4, 1986

INVENTOR(S) : Ward et al.                Page 1 of 2

It is certified that error appears in the above—identified patent and that said Letters Patent is hereby corrected as shown below:

Col. 2, line 58, after "fumaric" insert --,--.

Col. 3, line 11, "R40" should be --R'--.

Col. 7, line 6, "thereapeuitic" should be --therapeutic--.

Col. 7, line 12, "eczeme" should be --eczema--.

Col. 7, line 30, "of the propylaxis" should be --or the prophylaxis--.*

Col. 7, line 50, "orgal" should be --oral--.

Col. 8, line 44, "mmammals" should be --Mammals--.

Col. 10, line 41, "7-chloro-1H" should be --7-chloro-$\underline{1H}$--.

Col. 13, line 67, "7chloro" should be --7-chloro--.

UNITED STATES PATENT AND TRADEMARK OFFICE
CERTIFICATE OF CORRECTION

PATENT NO. : 4,621,089
DATED : November 4, 1986
INVENTOR(S) : Ward et al.   Page 2 of 2

It is certified that error appears in the above-identified patent and that said Letters Patent is hereby corrected as shown below:

Col. 14, line 43, "5.57 - 6.30" should be --5.75 - 6.30--.

Col. 16, line 41, "Swinge" should be --Swingle--.

Col. 16, line 47, "weight" should be --weighed--.

Col. 17, line 27, "X is sulphur SO or NR wherein R is hydrogen of $C_{1-6}$ alkyl, $SO_2$" should be --X is sulphur, SO, $SO_2$ or NR wherein R is hydrogen or $C_{1-6}$ alkyl--.

Col. 20, line 27, "adminstration" should be --administration--.

Signed and Sealed this

Twenty-seventh Day of October, 1987

Attest:

DONALD J. QUIGG

Attesting Officer

Commissioner of Patents and Trademarks